United States Patent [19]
Bookwalter et al.

[11] Patent Number: 5,320,314
[45] Date of Patent: Jun. 14, 1994

[54] BUILT-IN ENCLOSED STABILIZER POST OPERATING TABLE CLAMP

[76] Inventors: John R. Bookwalter, 9 Belmont Ave., Brattleboro, Va. 05301; William H. Bookwalter, 337 College St., Burlington, Vt. 05401

[21] Appl. No.: 7,915

[22] Filed: Jan. 22, 1993

[51] Int. Cl.⁵ .............................................. A47B 97/00
[52] U.S. Cl. .................... 248/231.4; 24/525; 248/214; 248/316.4
[58] Field of Search ............... 248/231.4, 316.4, 231.3, 248/316.2, 534, 214, 228, 231.2; 24/525

[56] References Cited

U.S. PATENT DOCUMENTS

| | | | |
|---|---|---|---|
| 1,342,870 | 6/1920 | Robichaux | 24/525 X |
| 2,749,196 | 6/1956 | Wolfe | 248/228 X |
| 3,243,153 | 3/1966 | Kelly et al. | 248/231.2 |
| 3,606,391 | 9/1971 | Sinnott | 24/525 X |
| 3,637,182 | 1/1972 | Bohlman | 248/231.4 |
| 4,018,412 | 4/1977 | Kees, Jr. et al. | 248/214 |
| 4,466,596 | 8/1984 | Cohen | 248/231.4 X |
| 4,971,038 | 11/1990 | Farley | 24/525 X |
| 5,169,106 | 12/1992 | Rasmussen | 248/231.4 X |

Primary Examiner—Karen J. Chotkowski
Attorney, Agent, or Firm—Donald W. Meeker

[57] ABSTRACT

The moving parts of the clamping mechanism are enclosed within a hollowed out enlarged casing at the base of the stabilizer post. The hooked base of the post forms the bottom of the clamp. Inside the post casing the hooked top of the clamp is attached to two side panels with angled slots. A screw through a back panel engages a large rectangular nut fitted with angled protruding blocks on each side of the nut. The nut protruding blocks fit into the angled slots of the side panels. The bolt is rotataly fixed at one end so turning it moves the nut forward and backward along the screw. When the bolt is turned and the nut moves horizontally on the bolt, the side panels move up and down. The hooked top of the clamp moves up or down engaging and releasing a side rail of an operating table between the clamp elements. A relatively flat knob to turn the screw is the only protrusion from the post casing at the base.

2 Claims, 1 Drawing Sheet

U.S. Patent     June 14, 1994     5,320,314
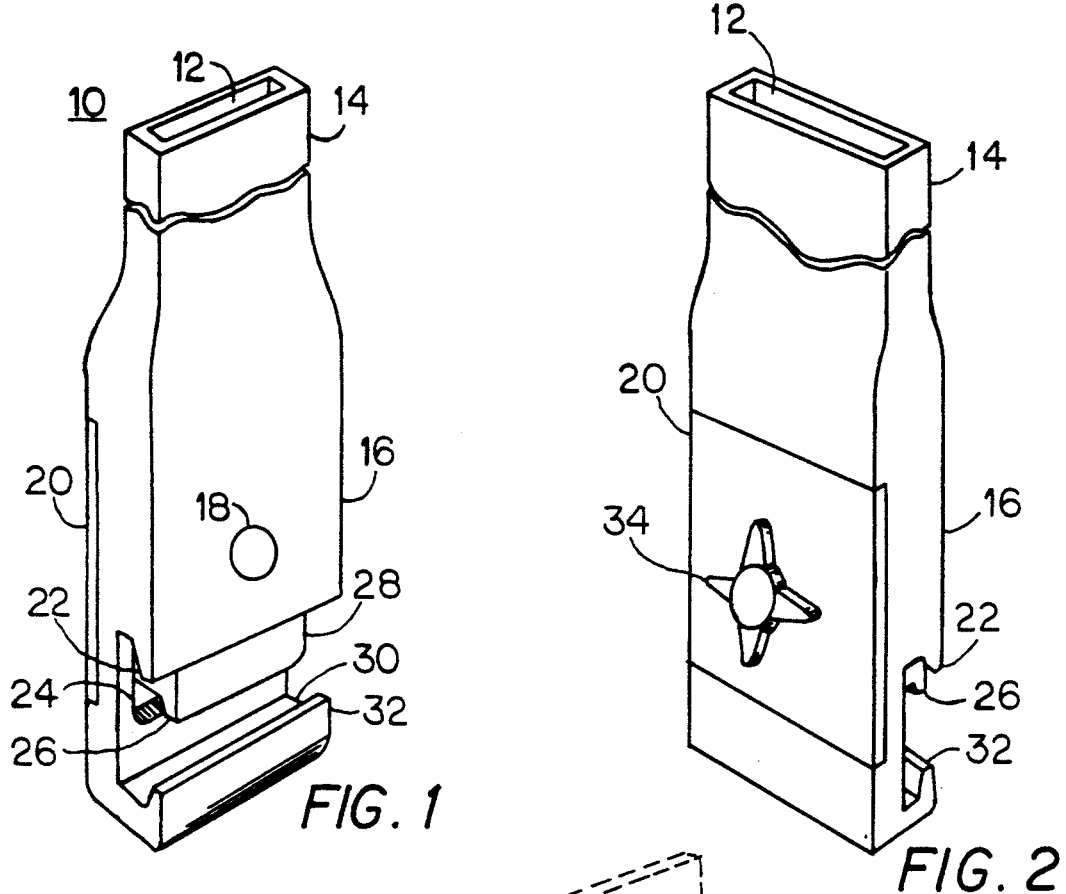
FIG. 1
FIG. 2
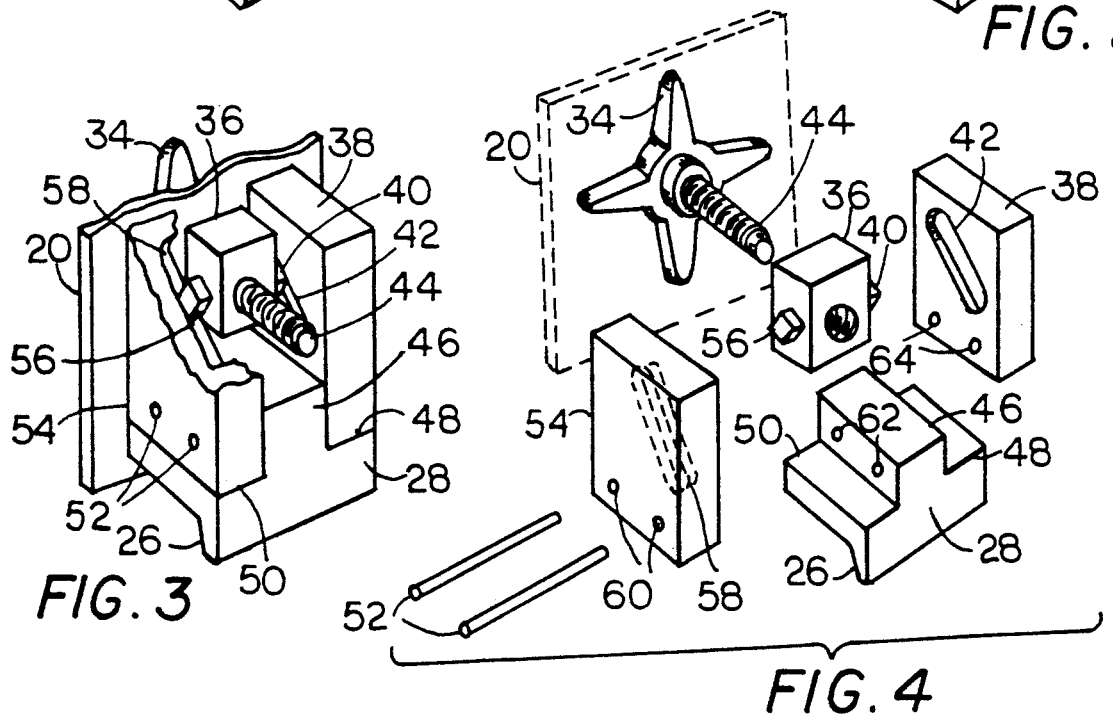
FIG. 3
FIG. 4

BUILT-IN ENCLOSED STABILIZER POST OPERATING TABLE CLAMP

BACKGROUND OF THE INVENTION

1. Technical Field

The present invention relates to clamping devices that support a surgical retractor apparatus, and in particular to an operating table clamp that is built into and enclosed within a stabilizer post for supporting surgical retractor apparatus.

2. Description of the Prior Art

In clamping a stabilizer post to an operating table it is important to have a rigid connection between the operating table and the stabilizer post to insure that no movement of the post will occur during an operation.

Another consideration in an operating room is maintaining a sterile environment. The more complex the apparatus used in an operating room environment, the more opportunity there is for contamination. Exposed threads on screws and other parts of complex mechanical equipment present contamination hazards as well as posing a hazard to the staff in the operating room in terms of bumping into protruding pieces of equipment.

Sterility problems also arise when stabilizer posts are clamped directly to the operating table rail and slits are cut in the surgical drape to accommodate the post, thereby violating the barrier between the sterilized exterior above the drape and the unsterilized interior below the drape. Moving the stabilizer post presents a sterilization problem under those conditions.

Prior art devices primarily have operating table clamping means in which the clamp is separate from the post with the post sliding through the clamp or inserted in the clamp. The connection between the table and the post is weakened by a double clamp (one screw to tighten onto the table and one screw to tighten onto the post) and potential for having a loose screw is increased in addition to the hazard of having protruding screws and exposed screw threads.

DISCLOSURE OF INVENTION

The present invention provides an operating table clamp built into and enclosed by the stabilizer post. The broad base of the stabilizer post is cut into a J-shaped to form the lower jaw of the clamp across the entire width of the post. The broad upper jaw almost as wide as the post moves downwardly under the force of a large screw and inclined plane system to rigidly engage a side rail of an operating table with no possibility of movement once the upper jaw is screwed down tight.

Movable elements forming the upper jaw are enclosed within the stabilizer post. Blood and biomatter cannot foul the movable elements and none of the elements could fall out should the mechanism break. Only a relatively flat knob to tighten the jaws creates a slight profile on the outer face of the stabilizer post but not protruding beyond the sides of the post. The screw threads to move the upper jaw are all contained within the post. This provides a smooth post with just the relatively flat knob outside of it, thereby creating a safer environment in terms of maintaining a sterile environment and an environment free of elements that operating room staff might get caught on or bump into.

The jaws grips the operating table side rail over the surgical drape eliminating sterility problems and enabling the post to be moved more easily. The clamp will fit a variety of different operating tables having side rails of slightly different thicknesses and widths.

BRIEF DESCRIPTION OF THE DRAWINGS

These and other details and advantages of our invention will be described in connection with the accompanying drawings, which are furnished only by way of illustration and not in limitation of the invention, and in which drawings:

FIG. 1 is a perspective view of the stabilizer post base with the built-in clamp showing the table side of the post with only the gripping jaws exposed;

FIG. 2 is a perspective view of the invention showing the opposite outer side with the flat handle exposed;

FIG. 3 is a partial perspective view of the inner workings of the clamp which move the upper jaw;

FIG. 4 is an exploded perspective view of the inner workings of the clamp.

BEST MODE FOR CARRYING OUT THE INVENTION

In FIGS. 1 and 2, a built-in enclosed stabilizer post operating table clamp 10 comprises a stabilizer post 14 having a base formed into a lower clamp jaw 32 by cutting out a groove 30 across the width of the post leaving a J-shaped hook. A hollow interior space 24 above the base inside the enlarged casing 16 houses the movable components of the upper jaw. A relatively flat know 34 outside the post on the outer side of a back plate 20 turns the screw.

A movable upper jaw 26 is formed by a lip extending downwardly from an upper jaw block 28 which is positioned within the hollow interior space of the casing 16.

In FIGS. 3 and 4 the upper jaw moving means comprises a screw and inclined plane mechanism. A screw 44 extends horizontally through the hollow interior space, which screw is fixed rotatably at an end of the screw 18 protruding through the front of the post casing 16. An enlarged rectangular nut 36 is threaded onto the screw so that as the screw turns reversibly, the nut moves forward and back along the screw. The enlarged nut 36 has a protrusion 40 and 56 on each of two opposing sides.

The upper jaw block 28 has a lower extending lip 26 along the front edge of the block and an upper rectangular ridge 46 extending transversely across the top of the block leaving side ridges 48 and 50. Two spaced rectangular elements 38 and 54 fit onto the ridges 48 and 50 on the sides of the upper rectangular ridge 46. Pins 52 fit through holes 60, 62 and 64 to secure the three components together. The two spaced rectangular elements 38 and 54 protrude above the block with parallel interior faces sandwiching the enlarged nut 36 between the faces. Each interior face has an angled slot 42 and 58 cut into it to receive the protrusions 40 and 56 from the nut in the angled slots 42 and 58, respectively.

Turning the screw 44 reversibly with the relatively flat knob 34 causes the nut 36 to move horizontally forward and back and the nut protrusions 40 and 46 in the angled slots 42 and 58 cause the upper jaw 26 to move up and down to clamp tightly onto side rails of operating tables of a variety of slightly different thicknesses and widths. An extension of the post may be fitted into a slot 12 at the top of the stabilizer post to which will be attached retractors or other surgical apparatus.

All of the components are preferably fabricated from stainless steel or other strong and sterilizable materials.

It is understood that the preceding description is given merely by way of illustration and not in limitation of the invention and that various modifications may be made thereto without departing from the spirit of the invention as claimed.

We claim:

1. A built-in enclosed stabilizer post operating table clamp comprising a stabilizer post having a base formed into a lower clamp jaw and a hollow interior space within an enlarged casing above the base;

an upper jaw positioned movably within the hollow space;

an upper jaw moving means for moving the upper jaw reversibly up and down, which upper jaw moving means is positioned within the interior space of casing;

wherein the upper jaw moving means comprises a screw and inclined plane mechanism;

wherein the screw and inclined plane mechanism comprises a screw extending horizontally through the hollow interior space, which screw is fixed rotatably to the enlarged casing on at least one end of the screw, and an enlarged rectangular nut threaded onto the screw, wherein the enlarged nut has a protrusion on each of two opposing sides, an upper jaw comprising a block having a lower extending lip and two spaced rectangular elements protruding above the block with parallel interior faces sandwiching the enlarged nut between the faces, wherein each interior face has an angled slot cut into it to receive the protrusions from the nut in the angled slots, and wherein turning the screw reversibly causes the nut to move horizontally forward and back and the nut protrusions in the angled slots cause the upper jaw to move up and down;

wherein the jaws engage a side rail on an operating table.

2. The invention of claim 1 wherein a relatively flat knob outside the post turns the screw.

* * * * *